United States Patent
Utech et al.

(10) Patent No.: US 10,372,880 B2
(45) Date of Patent: Aug. 6, 2019

(54) MANAGING RE-USE OF RETURNED MEDICATIONS

(71) Applicant: CareFusion 303, Inc., San Diego, CA (US)

(72) Inventors: Thomas William Utech, Dallas, TX (US); Maria Consolacion Jaskela, San Rafael, CA (US); William Lee Webster, Rockwall, TX (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 13/900,493

(22) Filed: May 22, 2013

(65) Prior Publication Data

US 2014/0350948 A1 Nov. 27, 2014

(51) Int. Cl.
*G06F 19/00* (2018.01)

(52) U.S. Cl.
CPC ................................ *G06F 19/3456* (2013.01)

(58) Field of Classification Search
CPC ..... G06Q 50/22–50/24; G06F 19/3456; G16H 20/10
See application file for complete search history.

(56) References Cited

U.S. PATENT DOCUMENTS

| | | |
|---|---|---|
| 6,202,923 B1 | 3/2001 | Boyer et al. |
| 8,027,749 B2 | 9/2011 | Vahlberg et al. |
| 8,239,062 B2 | 8/2012 | Vahlberg et al. |
| 2002/0198624 A1* | 12/2002 | Greenwald et al. .......... 700/231 |
| 2005/0096941 A1 | 5/2005 | Tong |
| 2006/0249423 A1 | 11/2006 | Reijonen |
| 2007/0185615 A1 | 8/2007 | Bossi et al. |
| 2008/0195416 A1 | 8/2008 | Tribble et al. |
| 2008/0319795 A1 | 12/2008 | Poteet et al. |
| 2010/0094653 A1 | 4/2010 | Tribble et al. |
| 2010/0161113 A1 | 6/2010 | Tribble et al. |
| 2010/0174552 A1 | 7/2010 | Hawkes et al. |
| 2013/0006652 A1 | 1/2013 | Vahlberg et al. |
| 2013/0018356 A1 | 1/2013 | Prince et al. |

(Continued)

OTHER PUBLICATIONS

"Introducing DoseEdge Pharmacy Workflow Manager," Baxter Healthcare Corporation, visited May 22, 2013, retrieved from <http://www.baxa.com/doseedge/>.

(Continued)

*Primary Examiner* — Sheetal R Paulson
(74) *Attorney, Agent, or Firm* — Morgan, Lewis & Bockius LLP (57) ABSTRACT

Methods for managing a return of a prepared medication are provided. In one aspect, a method includes receiving an identification of at least one returned medication delivered to a first location, and receiving an order for another medication. The method also includes determining whether the at least one returned medication is usable for completing the order of the other medication, and when the determination indicates that the at least one returned medication is usable for completing the order of the other medication, providing a notification indicating that the at least one returned medication is usable for completing the order of the other medication. Systems and machine-readable media are also provided.

23 Claims, 5 Drawing Sheets

(56) References Cited

U.S. PATENT DOCUMENTS

2013/0226600 A1* 8/2013 Barfield .......................... 705/2
2013/0262138 A1* 10/2013 Jaskela et al. ................... 705/2

OTHER PUBLICATIONS

International Search Report and Written Opinion in PCT Patent Application No. PCT/US2014/039228 dated Aug. 22, 2014, 11 pgs.
Extended European Search Report for Application No. 14801015.0, dated Jan. 12, 2017, 8 pages.
Memo concerning Mexican Office Action for Application No. MX/a/2015/016011, memo dated Oct. 4, 2017, 3 pages.
Memo concerning Mexican Office Action for Application No. MX/a/2015/016011, memo dated Apr. 6, 2018, 3 pages.
Chinese Office Action for Application No. 201480041659.X, dated May 10, 2019, 7 pages.
Australian Office Action for Application No. 2014268476, dated Feb. 13, 2019, 4 pages.

* cited by examiner

MANAGING RE-USE OF RETURNED MEDICATIONS

BACKGROUND

Field

The present disclosure generally relates to medication distribution, and, in particular, relates to systems and methods for managing re-use of returned medication in a healthcare facility.

Description of the Related Art

Certain pharmaceutical drugs are compounded to fit the needs of a patient. Compounding pharmacists combine or process appropriate ingredients using various tools to create a compounded pharmaceutical drug. For instance, compounding of sterile intravenous (IV) compounds can be done in anticipation of medication orders based on standard doses, or compounding can be done specific to a patient's need based on a physician order. Compounding may be done for medically necessary reasons, such as to change the form of the medication from a solid pill to a liquid, to avoid a non-essential ingredient that the patient is allergic to, or to obtain the exact dose(s) needed of particular active pharmaceutical ingredient(s). It may also be done for more optional reasons, such as adding flavors to a medication or otherwise altering taste or texture. Compounding is most routine in the case of intravenous (IV)/parenteral medication IV fluid delivery systems are used to deliver such compounded IV medications (or "infusion solutions") in fluid form to patients at controlled rates. Many individuals suffer from acute and chronic health problems, the treatment of which could require regular, and sometimes extended, IV infusions. Certain treatment regimens for diseases such as infections, cancer and even basic fluid and electrolyte replacement, require a regular and sequenced infusion of precise amounts of intravenous medication for the patient's survival. Specifics of intravenous infusion of medications may depend on the patient, treatment regimen, and choices of the clinician and institution. Treating chronic medical disorders often requires the administration of medication over a long period of time according to a treatment regimen specified by a medical professional, such as a physician.

In cases of patients admitted to a healthcare facility, one or more infusions to be administered to a patient are prescribed by the patient's physician. A pharmacy, generally located within the patient's hospital or healthcare facility, prepares the infusion medication or solution according to the physician's prescription, for example, in a cleanroom (e.g., an environment having a controlled level of contamination that is specified by a number of particles per cubic meter at a specified particle size). An appropriately trained and credentialed pharmacist places the infusion solution in a bag, bottle, syringe, or other container and labels the container. The infusion solution is then commonly staged in a pickup location, such as a bin-sorting area. A sorting person is then responsible for placing each prepared infusion solution into bins or delivery carts that correspond to the locations where the infusion solutions will be delivered, such as an Intensive Care Unit (ICU). A delivery person retrieves the infusion solutions from the bins that correspond to areas of the healthcare facility to which that delivery person delivers. The delivery person then delivers the infusion solutions to the appropriate locations of the healthcare facility.

The infusion solution is then delivered to the patient's location and a clinician such as a nurse or other clinician hangs the infusion solution from a rack. The nurse connects a tube between the infusion solution and an infusion pumping system and inserts a cannula at the end of the tube into the vessel of the patient for delivery of the infusion solution to the patient.

SUMMARY

According to certain embodiments of the present disclosure, a system for managing a return of a prepared medication is provided. The system includes a memory that includes instructions, and one or more processors. The one or more processors are configured to execute the instructions to receive an identification of at least one returned medication delivered to a first location, and receive an order for another medication. The one or more processors are also configured to execute the instructions to determine whether the at least one returned medication is usable for completing the order of the other medication, and when the determination indicates that the at least one returned medication is usable for completing the order of the other medication, provide a notification indicating that the at least one returned medication is usable for completing the order of the other medication.

According to certain embodiments of the present disclosure, a method for managing a return of a prepared medication is provided. The method includes receiving an identification of at least one returned medication delivered to a first location, and receiving an order for another medication. The method also includes determining whether the at least one returned medication is usable for completing the order of the other medication, and when the determination indicates that the at least one returned medication is usable for completing the order of the other medication, providing a notification indicating that the at least one returned medication is usable for completing the order of the other medication.

According to certain embodiments of the present disclosure, a machine-readable storage medium that includes machine-readable instructions for causing a processor to execute a method for managing a return of a prepared medication is provided. The method includes receiving an identification of at least one returned medication delivered to a first location, and receiving an order for another medication. The method also includes determining whether the at least one returned medication is usable for completing the order of the other medication, and when the determination indicates that the at least one returned medication is usable for completing the order of the other medication, providing a notification indicating that the at least one returned medication is usable for completing the order of the other medication.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The disclosed system provides a delivery person who is delivering infusion solutions to a particular area of a healthcare facility with a list of discontinued infusion solutions and their location in the area to which the delivery person is delivering. The delivery person may then retrieve the discontinued infusion solutions and return them to a pharmacy location providing services within a facility. The discontinued infusion solutions may be scanned upon their return to the pharmacy and listed in an inventory of available infusion solutions. In certain aspects, the discontinued infusion solutions may be scanned when initially retrieved by the delivery person and also be listed in the inventory of available solutions. If the discontinued infusion solutions have passed their expiration date, or are not within a threshold time duration of their expiration date, e.g., exceeding the amount of time required to deliver to and administer the infusion solution at another location, then the discontinued infusion solutions are discarded. However, if the discontinued infusion solutions are not within the threshold time duration of their expiration date, the discontinued infusion solutions are re-entered into inventory for possible re-use. In certain aspects, the expiration date of an infusion solution can be automatically determined based on the stability and sterility of the medication.

When a new order for an infusion solution is received, the disclosed system first checks whether the discontinued infusion solution that has been re-entered into inventory can be used to fill the new order. If the order can be filled with the discontinued infusion solution, then the discontinued infusion solution is used for the order. However, if the order cannot be filled with the discontinued infusion solution, then the order is placed in an infusion solution preparation queue for preparation by a technician or pharmacist.

In certain aspects, the disclosed system may determine one or more metrics regarding the number of discontinued infusion solutions that are re-entered into inventory and/or the number of discontinued infusion solutions that are discarded. The disclosed system may, for example, utilize the one or more metrics to adjust a suggested number of infusion solutions that are prepared without any corresponding orders on a daily basis, e.g., the number of fast mover pre-pack infusion solutions that are prepared on a daily basis. For example, if a large number of discontinued orders for a particular fast mover pre-pack infusion solution is being re-entered into inventory on a daily basis, and the fast mover pre-pack infusion solutions subsequently expire before they can be administered to a patient, the disclosed system may reduce the suggested number of the fast mover pre-packs that should be prepared on a daily basis.

Figure 1:
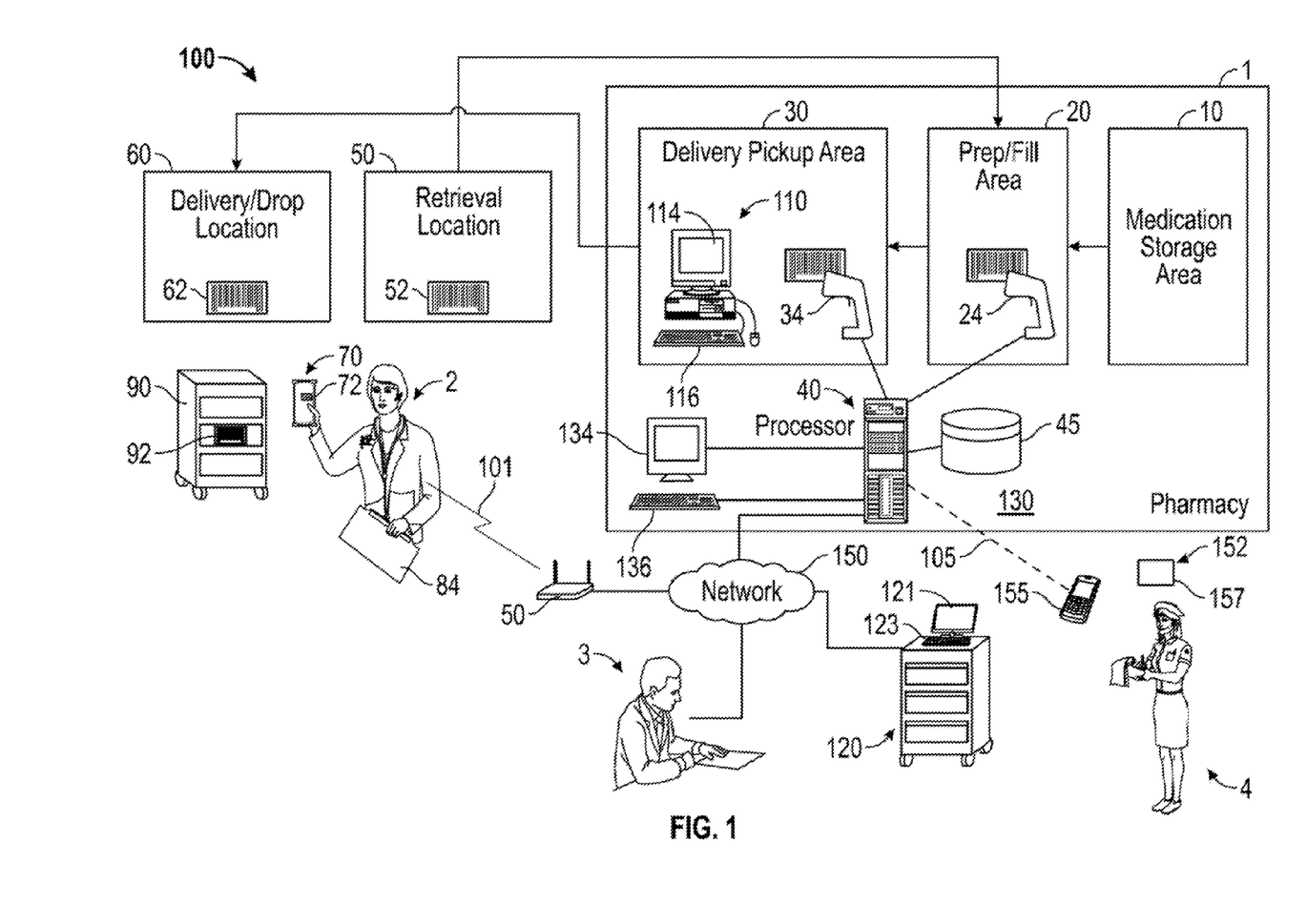
FIG. 1 illustrates an example architecture for managing a return of a prepared medication.

Turning now to the drawings, FIG. 1 illustrates an example architecture 100 for managing a return of a prepared medication according to certain aspects of the present disclosure. For ease and clarity of illustration only, without any intent to limit the scope of the present disclosure any way, it is assumed that the prepared medication provided as an example for FIG. 1 is an anesthetic IV solution.

The architecture 100 includes a pharmacy 1 having a medication storage area 10, a fill and/or preparation (fill/prep) area 20, and a delivery pickup area 30 (e.g., bin-sorting area). The medication storage area 10 includes a plurality of medications and supplies including, for example, an anesthetic drug (e.g., bupivacaine or chloroprocaine) and an appropriate fluid for the anesthetic drug. The anesthetic drug and the fluid are taken from the medication storage area 10 to the prep/fill area 20 where they are mixed together to produce the anesthetic IV solution. A patient/medication ID device 72, such as a barcode label or a radio frequency identification (RFID) tag, is provided on (e.g., affixed to) a package 70 (e.g., IV bag) containing the IV solution at the prep/fill area 20. The patient/medication ID device 72 includes patient/medication ID information indicative of the medication and the patient to whom the medication is prescribed. The package 70 is then taken by a technician at the pharmacy 1 to the delivery pickup area 30. The technician determines an appropriate bin or delivery cart 90 into which to place the package 70, and then loads the package 70 onto the appropriate delivery cart 90 for delivery to a scheduled delivery/drop location 60 (e.g., a patient room) by a delivery person 2.

In the illustrated embodiment, the prep/fill area 20 has a barcode reader 24 provided therein that the technician at the pharmacy 1 can use to read the patient/medication ID device 72 (a barcode label in the illustrated example) before the package 70 is taken to the delivery pickup area 30. The delivery pickup area 30 has a barcode reader 34 connected to a client 110 provided therein that the technician at the pharmacy 1 can use to read the patient/medication ID device 72 once the package 70 is taken to the delivery pickup area 30. The delivery cart 90 may also be provided with a location barcode label reader. The delivery person 2 can use the barcode reader 34 to scan the package 70 to indicate the delivery person 2 will begin delivery of the package 70.

The pharmacy 1 includes a server 130 (e.g., pharmacy server) that includes a processor 40. The server 130 is coupled to an output device 134, such as a display, and an input device 136, such as a keyboard. The server 130 can be any device having an appropriate processor, memory, and communications capability for receiving, processing, and sending information associated with a medication database 45 and prepared medications. The processor 40 is coupled to the medication database 45 that is configured to store a variety of information including order status information and delivery progress information to be discussed below. The processor 40 is configured to receive an identification of a returned package 70 (e.g., at the prep/fill area 20) and determine, based on the expiration date of the returned package 70, whether the returned package 70 should be discarded, or kept for use in filling another potential order.

The processor 40 is configured to determine an expiration date for the returned package 70 based on, for example, the stability and sterility of the returned package 70. Information indicative of the stability and sterility of the returned package 70 may be obtained from the medication database 45. For example, the stability of the returned package 70, which indicates a length of time a drug in the returned package 70 retains its properties without loss of potency (i.e., "shelf life") can initially be entered by a pharmacist or other health care provider when the returned package 70 is first prepared. The sterility of the returned package, which indicates the conditions in which the package 70 was prepared (e.g., an environment particle count), can be determined based on a known location in which the package 70 was prepared as stored in the medication database 45. For instance, if the package returned package 70 is prepared in a sterile zone, it may be given a longer expiration time flame than if the returned package 70 were not prepared in a sterile zone. The processor 40, based on a stability date entered by a pharmacist and a sterility indicator calculated based on the known location in which the package 70 was prepared, can then generate an expiration date for the returned package 70.

The processor 40 may also identify a location (e.g., retrieval location 50, such as a first patient room) of a discontinued package 70 that is ready for return, and provide the identification of the discontinued package 70 and of the retrieval location 50 to a client 110 for display on an output device 114 at or near the delivery pickup area 30 instructing the delivery person 2 to retrieve the discontinued package 70 from the retrieval location 50. The client 110 can be, for example, a computer system associated with the delivery pickup area 30 such as a desktop computer or mobile computer. The client 110 can also be, for example, a tablet computer, mobile device (e.g., a smartphone or PDA), or any other device having appropriate processor, memory, and communications capabilities. The mobile device may, for example, be associated with the delivery person 2.

The processor 40 is further configured to receive a new order for medication (e.g., from a doctor 3) for delivery to a delivery/drop location 60, and determine whether the new order for the medication can be filled using a returned prepared medication. The processor 40 is yet further configured to provide a notification, e.g., to output device 134 in the pharmacy 1, as to whether the new order can be filled using a returned prepared medication. For example, a notification can be displayed on the output device 134 indicating that a returned prepared medication for bupivacaine IV solution and be used to fill a new order for bupivacaine IV solution.

The delivery location 60 and/or the retrieval location 50 can include, for example, patient rooms having an infusion device for providing an IV infusion from a package to a patient. In the illustrated example, the retrieval location 50 and the delivery location 60 are provided with location barcode label 52 and location barcode label 62, respectively. Each of the location barcode labels 52, 62 includes unique location ID information indicative of the respective location 50, 60 where the corresponding barcode label is provided. As described above, the package 70 (e.g., IV bag) containing the medication (e.g., IV solution) is provided with a patient/medication identification (ID) device 72. In the illustrated example, the patient/medication ID device 72 is a barcode label that includes patient/medication information indicative of the patient (e.g., "Jane Smith") and the medication (e.g., "bupivacaine IV solution"). The patient/medication information may also contain other drug or patient related information such as the patient's medical conditions (e.g., allergies), name of the drug (e.g., bupivacaine), the drug dosage, the drug concentration, the drug administration schedules, and the drug administration rate.

Also depicted in the architecture 100 of FIG. 1 is a reader device 84 that is hand carried by the delivery person 2 and/or attached to the delivery cart 90 and is configured to read the patient/medication information from the patient/medication ID device 72 provided on the package 70. In the illustrated example, the reader device 84 is a barcode scanner. In those embodiments in which the barcode scanner 84 is hand carried by the delivery person 2, the scanner 84 is also configured to read the location ID information from the location barcode labels 52, 62, 92.

In the embodiments described above, the location ID devices 52, 62, 92 and/or the patient/medication ID device 72 are passive ID devices, meaning that certain action (e.g., scanning) has to be taken by the participant (e.g., a pharmacy technician or the delivery person 2) to retrieve information therefrom. In other embodiments, the ID devices can be active ID devices, meaning that the information retrieval from the ID devices occur automatically without an action taken by the participant. In some embodiments, the active ID devices can actively transmit signals containing the relevant information to the reader device 72 through a wireless link. The wireless link can use a variety of technologies including Bluetooth, ZigBee, wireless USB, and proprietary systems. In other embodiments, the active ID devices do not themselves transmit signals, but respond to query signals generated by a reader device (e.g., by altering impedance of an RF circuit therein) as the reader device passes by the ID devices in close proximity.

In the illustrated example, each time the barcode scanner 84 scans an ID device (e.g., patient/medication ID device or location ID device), the information read thereby is wirelessly transmitted to a wireless bridge 50 that receives the information. The bridge 50 is in data communication with the processor 40 via a hospital network 150. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

The processor 40 is configured to receive medication/patient ID information and/or location ID information read by the barcode scanner 84, generate location, use, and re-use information therefrom, and store the information in the medication database 45. The medication database 45 can include information such as, but not limited to: the patient's name or ID, the medication name or ID, the scheduled delivery location 60, the scheduled delivery time, an expiration date or time for a prepared medication, an urgency of delivery of the prepared medication, a current location of the prepared medication, an order status of the prepared medication, a return status of the prepared medication, one or more read locations where the medication/patient ID information and/or the location ID information was read by the barcode scanner 84, time when the information was read, and the name or ID of the delivery person 2.

The architecture 100 further comprises tracking devices 120, 152 that allow a care provider 4 (e.g., a nurse assigned the task of administering the patient-specific medication to the patient) to monitor the progress of the delivery of the medication. Each of the tracking devices 120, 152 is configured to receive a tracking request by the care provider 4, access the medication database 45, either directly or via the processor 40, retrieve the delivery progress information stored in the database 45, and indicate a delivery progress of the medication to the care provider 4 based on the delivery progress information. In the illustrated example, the tracking device 120 is an automated dispensing machine having a processor (not shown), a display 121, and a keyboard 123; and the tracking device 152 is a mobile communication device (e.g., a cell phone, personal digital assistant (PDA), or pager) having a processor (not shown), a display 151, and a keyboard 153. The delivery progress information can inform the care provider 4 of a last-known read location and time of the last reading. Based on such information, the care provider 4 can decide, e.g., whether to wait for the delivery at the delivery location 60, go to the delivery location later at an expected delivery time, or go to the last-known location to retrieve the medication from the cart 90.

Figure 2:
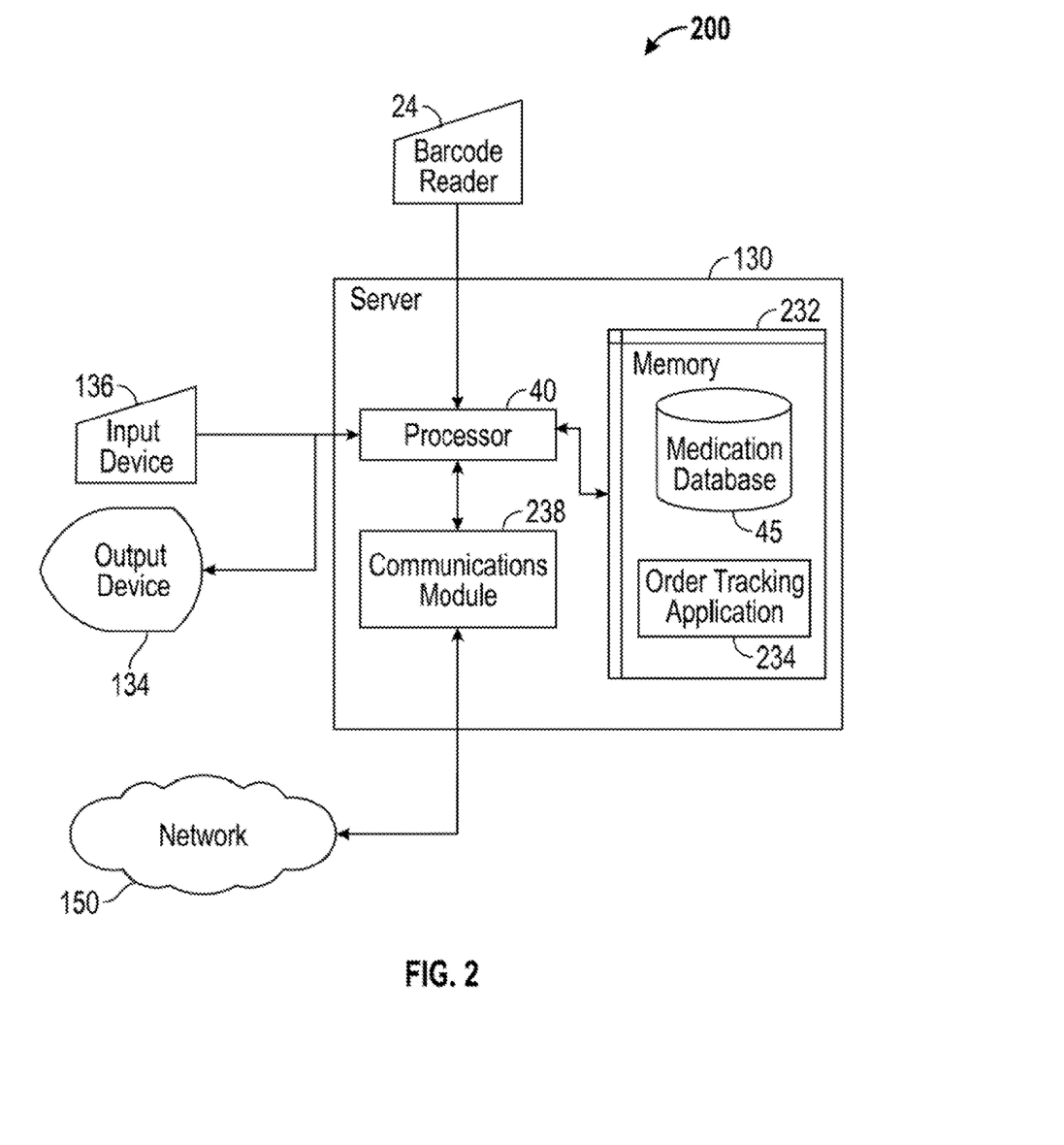
FIG. 2 is a block diagram illustrating an example server from the architecture of FIG. 1 according to certain aspects of the disclosure.

FIG. 2 is a block diagram 200 illustrating an example server 130 in the architecture 100 of FIG. 1 according to certain aspects of the disclosure. The server 130 is connected to the network 150 via a communications module 238. The communications module 238 is configured to interface with the network 150 to send and receive information, such as data, requests, responses, and commands to other devices on the network. The communications module 238 can be, for example, a modem or Ethernet card.

The server 130 includes the processor 40, the communications module 238, and a memory 232 that includes a medication database 45 and an order tracking application 234. The processor 40 of the server 130 is configured to execute instructions, such as instructions physically coded into the processor 236, instructions received from software in memory 240, or a combination of both. For example, the processor 236 of the server 130 executes instructions from the order tracking application 234 to receive an identification of at least one returned medication (e.g., package 70) delivered to a first location, such as the prep/fill area 20. The identification can be generated, for example, when the returned medication is scanned by the barcode reader 24 at the prep/fill area 20. For instance, when a delivery person 2 returns to the prep/fill area 20 with a medication, a barcode label 72 of the medication can be scanned by the barcode reader 24 in order to indicate that the medication has been returned to the prep/fill area 20.

The processor 40 of the server 130 is also configured to execute the instructions to provide, for display (e.g., to the output device 114 of the client 110), an identification of a location at which a medication to be returned is located (e.g., retrieval location 52) for retrieval so that the medication can be returned to the prep/fill area 20. For example, the processor 40 can send a message to a mobile device client 110 of the delivery person 2 indicating a location of a package 70 that should be retrieved and returned to the prep/fill area 20.

When the processor 40 receives an order for another medication, the processor 40 is configured to determine whether the returned medication is usable for completing the order of the other medication. The determination can be based on, for example, a comparison between at least two of an expiration time of the at least one returned medication, an estimated amount of time for delivering the at least one returned medication to a second location (e.g., delivery/drop location 60), an estimated time at which the at least one returned medication will be administered to a patient at the second location, and a delivery deadline for the other medication.

For example, if the returned medication is estimated to expire in ten minutes, and it is estimated to take thirty minutes to deliver the returned medication to the delivery/drop location 60, then the determination may indicate that the returned medication cannot be used for completing the order of the other medication. As another example, if the order for the other medication must be delivered to the delivery/drop location 60 within thirty minutes, and the estimated time to deliver the returned medication to the delivery/drop location 60 is one hour, then the determination may indicate that the returned medication cannot be used for completing the order of the other medication. As yet another example, if the returned medication is estimated to expire in one hour, it is estimated to take thirty minutes to deliver the returned medication to the delivery/drop location 60, and the order for the other medication must be delivered to the delivery/drop location 60 within forty-five minutes, then the determination may indicate that the returned medication can be used for completing the order of the other medication.

Accordingly, the processor 40 is configured to provide a notification indicating that the returned medication is usable for completing the order of the other medication when the determination indicates that the returned medication is usable for completing the order of the other medication. The notification can include, for example, an instruction to assist with preparation of the order of the other medication using the at least one returned medication. For instance, the notification can indicate that the returned medication should be combined with another returned medication to fill the order. As an example, if two returned medications are each for Cefazolin (2 gm/NS 50 ml), and a new order for Cefazolin (4 gm/NS 100 ml) is received by the processor 40, then the processor 40 can send a notification (e.g., to the output device 134) indicating that the two returned medications of Cefazolin (2 gm/NS 50 ml) should be combined to fill the new order for Cefazolin (4 gm/NS 100 ml).

Similarly, the processor 40 may be configured to provide a notification indicating to proceed with completing the order of the other medication when the determination indicates that the returned medication is not usable for completing the order of the other medication. For example, if the order for the other medication must be delivered to the delivery/drop location 60 within thirty minutes, and the estimated time to deliver the returned medication to the delivery/drop location 60 is one hour, then a notification on the output device 134 can indicate that the returned medication cannot be used for completing the order of the other medication. In certain aspects, the same notification or another notification can be provided by the processor 40 indicating the returned medication is expired, or the returned medication will expire within a threshold time period. The threshold time period may be based on an expiration time of the returned medication and an estimated amount of time for delivering the returned medication to the delivery/drop location 60.

In certain aspects, the processor 40 is configured to receive an identification of multiple medications returned to the first location (e.g., the prep/fill area 20) within a time period. The multiple returned medications may have been prepared, for example, in response to a recurring order to prepare medications that includes a number of the medications to be prepared. For example, the medication database 45 may include an order to prepare twenty IV bags of Vancomycin (1 gm/NS 50 ml) every day. The processor 40 may determine, based on at least one of a frequency of return of the medications, a total number of medications returned within the time period, and a frequency of expiration of the returned medications prior to delivery to the delivery/drop location 60, whether to modify the recurring order. For example, the processor 40 may identify that, on average, ten of the twenty prepared IV bags of Vancomycin (1 gm/NS 50 ml) are returned and discarded every day. The processor 40 may then modify the number of medications to be prepared based on the determination. For example, if the processor 40 identifies that, on average, ten of the twenty prepared IV bags of Vancomycin (1 gm/NS 50 ml) are returned and discarded every day, then the processor 40 may modify the recurring order in the medication database 45 to indicate that ten, not twenty, IV bags of Vancomycin (1 gm/NS 50 ml) should be prepared every day.

Figure 3:
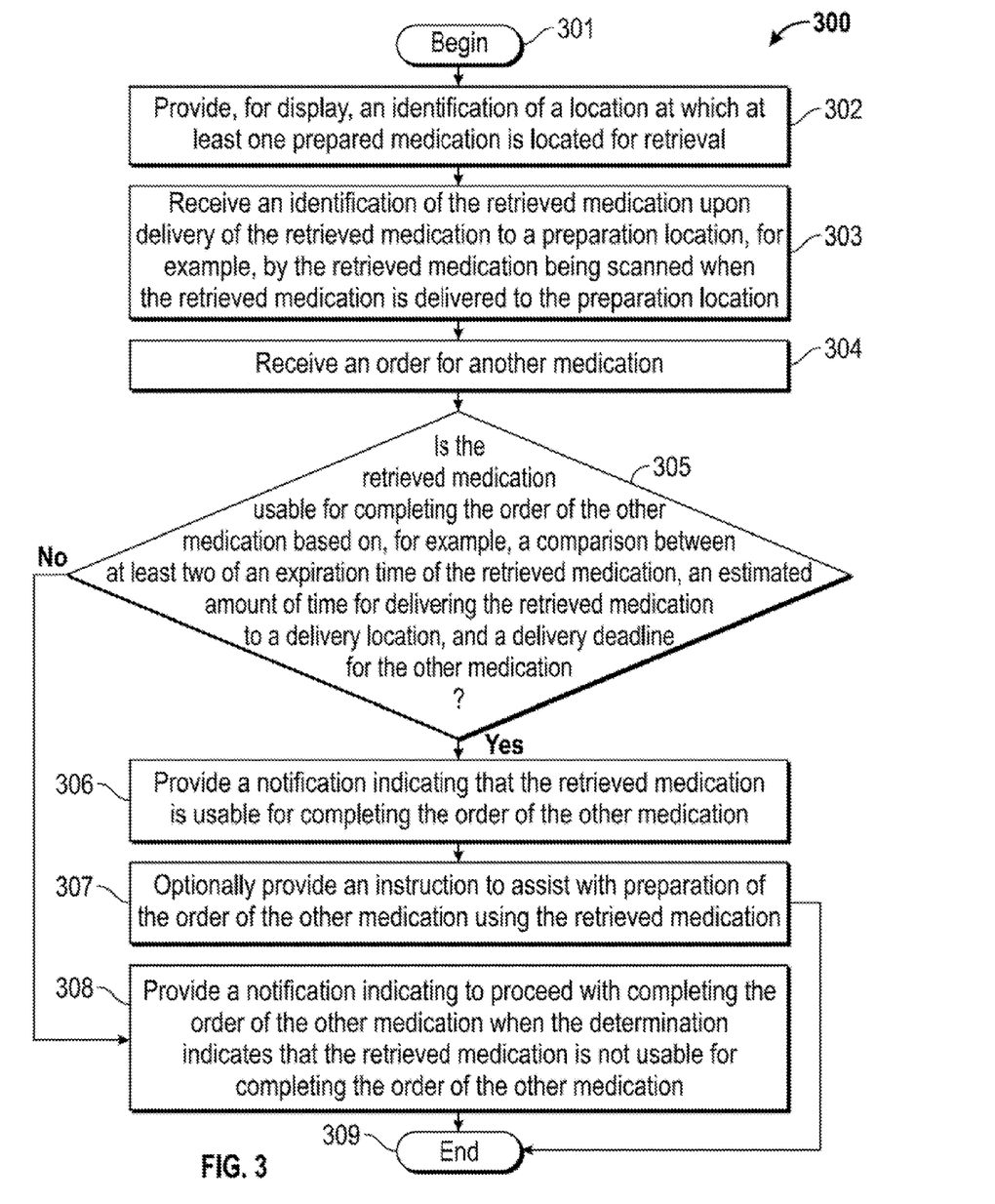
FIG. 3 illustrates an example process for managing a return of a prepared medication using the server of FIG. 2.

FIG. 3 illustrates an example process 300 for managing a return of a prepared medication using the example server 130 of FIG. 2. While FIG. 3 is described with reference to FIG. 2, it should be noted that the process steps of FIG. 3 may be performed by other systems.

The process 300 begins by proceeding from beginning step 301 to when a prepared medication is identified for retrieval to step 302 when the server 130 provides, for display (e.g., on client 110), an identification of a location at which the prepared medication is located for retrieval. Next, in step 303, an identification of the retrieved prepared medication is received upon delivery of the retrieved medication to the preparation location (e.g., prep/fill area 20), for example, when the retrieved prepared medication is scanned (e.g., using bar code reader 24) at the preparation location.

In step 304, an order for another medication is received. In decision step 305, a determination is made whether the retrieved medication is usable for completing the order of the other medication (e.g., of step 304) based on, for example, a comparison between at least two of an expiration time of the retrieved medication, an estimated amount of time for delivering the retrieved medication to a delivery location, and a delivery deadline for the other medication.

If the determination of decision step 305 indicates that the retrieved medication is usable for completing the order of the other medication, then the process 300 proceeds to step 305 in which a notification is provided indicating that the retrieved medication is usable for completing the order of the other medication. Next, in optional step 306, an instruction to assist with preparation of the order of the other medication using the retrieved medication is optionally provided. The process 300 then ends in step 309.

If the determination of decision step 305 indicates that the retrieved medication is not usable for completing the order of the other medication, then the process 300 proceeds to step 307 in which a notification is provided indicating to proceed with completing the order of the other medication. The process 300 then ends in step 309.

FIG. 3 set forth an example process 300 for managing a return of a prepared medication using the example server 130 of FIG. 2. An example will now be described using the example process 300 of FIG. 3 and a new order for Cefazolin (2 gm/NS 50 ml).

The process 300 begins by proceeding from beginning step 301 to when a prepared medication, Cefazolin (2 gm/NS 50 ml) expiring at 10:00 PM, is identified for retrieval from a retrieval location 50, patient room 3NW-5, to step 302 when the server 130 provides, for display (e.g., on a mobile device client 110 of a delivery person 2), an identification of the retrieval location 50 for the Cefazolin (2 gm/NS 50 ml). After the delivery person 2 retrieves the Cefazolin (2 gm/NS 50 ml) and arrives at the prep/fill area 20, then in step 303, an identification of the retrieved Cefazolin (2 gm/NS 50 ml) is received by the server 130 when the retrieved Cefazolin (2 gm/NS 50 ml) is scanned using the bar code reader 24 at the prep/fill area 20.

In step 304, a new order for Cefazolin (2 gm/NS 50 ml) to be delivered to delivery/drop location 60, patient room 5E-12, by 8:00 AM is received. In decision step 305, a determination is made whether the retrieved Cefazolin (2 gm/NS 50 ml) is usable for completing the new order of Cefazolin (2 gm/NS 50 ml) of step 304 based on a comparison between the expiration time of the retrieved Cefazolin (2 gm/NS 50 ml), 10:00 PM, an estimated amount of time for delivering the retrieved Cefazolin (2 gm/NS 50 ml) to delivery/drop location 60, thirty minutes, and a delivery deadline of 8:00 AM for delivering the Cefazolin (2 gm/NS 50 ml) to delivery/drop location 60.

The determination of decision step 305 indicates that the retrieved Cefazolin (2 gm/NS 50 ml) from patient room 3NW-5 is usable for completing the new order of Cefazolin (2 gm/NS 50 ml) for patient room 5E-12, so the process 300 proceeds to step 305 in which a notification is provided on the output device 134 of the server 130 indicating that the retrieved Cefazolin (2 gm/NS 50 ml) from patient room 3NW-5 is usable for completing the new order of Cefazolin (2 gm/NS 50 ml) for patient room 5E-12.

Figure 4:
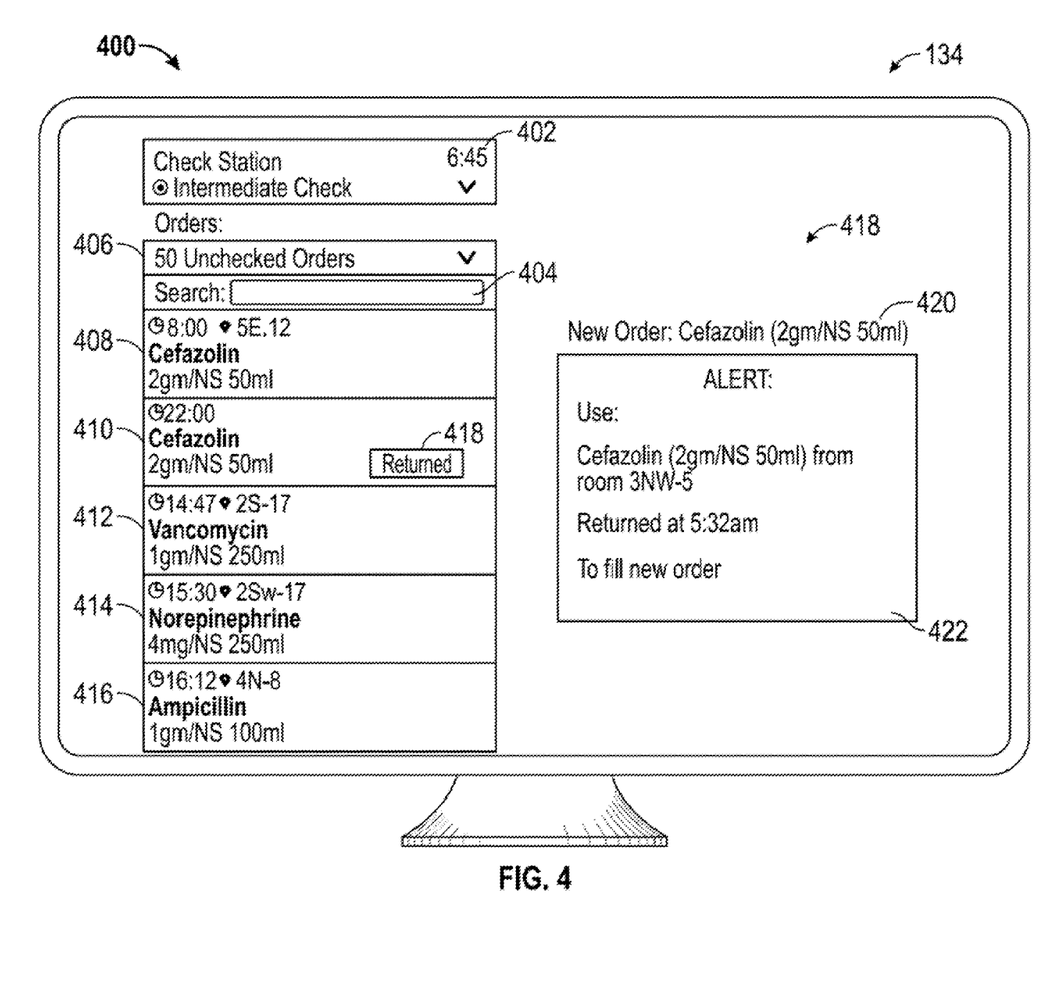
FIG. 4 is an example illustration associated with the example process of FIG. 3.

FIG. 4 provides an example illustration 400 of a graphical user interface for displaying the notification on the output device 134 of the server 130. The graphical user interface includes an identification of the current time 402, 6:45 AM, and a list of 50 unchecked orders 406 that may be sorted by, for example, priority, due time, location, or alphabetically and may be searched using a search interface 404. Five orders 408, 410, 412, 414, and 416 are listed and additional orders may be viewed by scrolling the interface below the five listed orders 408, 410, 412, 414, and 416. For each order, a due time, patient location, medication information, level of priority, and return status may be indicated. For example, the first order 408 listed identifies the medication as Cefazolin (2 gm/NS 5 ml) to be delivered to patient room 5E-12 by 8:00 AM. The second order 410 listed identifies that the medication Cefazolin (2 gm/NS 5 ml) has been returned 418, and has an expiration time of 10:00 PM.

The user interface also includes a messages area 418 that identifies 420 the new order of medication of step 304, namely the order for Cefazolin (2 gm/NS 5 ml) to be delivered to patient room 5E-12 by 8:00 AM, but also includes a notification 422 (of step 306) to be read by the pharmacist filling the new order. The notification 422 indicates to the pharmacist that that the second listed order 410, Cefazolin (2 gm/NS 50 ml) returned from patient room 3NW-5 at 5:32 AM, may be used to fill the new order for Cefazolin (2 gm/NS 5 ml). The process 300 then ends in step 308.

An instruction may optionally be displayed in step 306 to assist the pharmacist with preparation of the order of the other medication using the retrieved Cefazolin (2 gm/NS 50 ml). The instruction can be, for example, a statement indicating that the retrieved Cefazolin (2 gm/NS 50 ml) does not need to be altered to fill the new order for Cefazolin (2 gm/NS 50 ml). The process 300 then ends in step 309.

Figure 5:
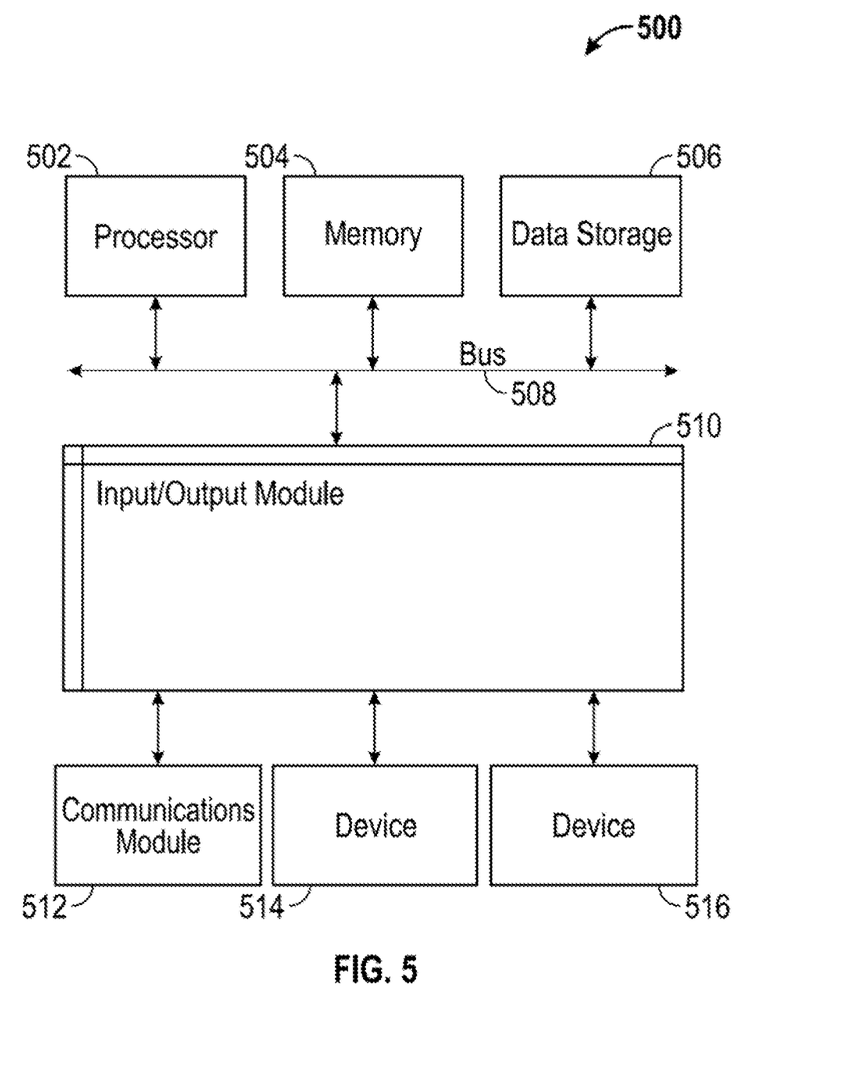
FIG. 5 is a block diagram illustrating an example computer system with which the server of FIG. 2 can be implemented.

FIG. 5 is a block diagram illustrating an example computer system 500 with which the server 130 of FIG. 2 can be implemented. In certain aspects, the computer system 500 may be implemented using hardware or a combination of software and hardware, either in a dedicated server, or integrated into another entity, or distributed across multiple entities.

Computer system 500 (e.g., server 130) includes a bus 508 or other communication mechanism for communicating information, and a processor 502 (e.g., processor 40) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 232), such as a Random Access Memory (RAM), a flash memory, a Read Only Memory (ROM), a Programmable Read-Only Memory (PROM) an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices (e.g., barcode reader 24). The input/output module 510 can be any input/output module. Example input/output modules 510 include data ports such as USB ports. The input/output module 510 is configured to connect to a communications module 512. Example communications modules 512 (e.g., communications module 238) include networking interface cards, such as Ethernet cards and modems. In certain aspects, the input/output module 510 is configured to connect to a plurality of devices, such as an input device 514 (e.g., input device 136) and/or an output device 516 (e.g., output device 134). Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the and server 130 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system, comprising:
   a display;
   a server; and
   a reader device configured to automatically receive identification information via a signal generated and transmitted wirelessly from an active identification device affixed to a moveable object when the identification device affixed to the moveable object is within a proximity of the reader device, and to transmit the identification information to the server, wherein the server comprises:
  a memory comprising instructions; and
  one or more processors configured to execute the instructions to:
    identify at least one medication at a first location within a healthcare facility, to be returned to a second location within the healthcare facility;
    provide, for display at a computing device associated with the first location and remote from the server, instructions to retrieve the identified at least one medication from the first location;
    receive, based on second information scanned from an active identification device affixed to the at least one medication and received wirelessly from the reader device without a scanning action taken by a participant, an indication of the at least one medication and that the at least one medication is available for re-use before it is returned to the second location;
    determining, based on the received indication and the second information, an expiration time for the at least one returned medication;
    receive an order for another medication, the order including a delivery deadline and a delivery location;
    determine, based on the delivery location and the received indication, a delivery time to deliver the order to the delivery location from the second location;
    determine, based on the expiration time, the delivery time, and the delivery deadline, whether the at least one returned medication is usable for completing the order of the other medication by the delivery deadline; and
    when the determination indicates that the at least one returned medication is usable for completing the order of the other medication, provide a notification on the display indicating that the at least one returned medication is usable for completing the order of the other medication.

2. The system of claim 1, wherein the one or more processors is further configured to execute the instructions to provide a notification indicating to proceed with completing the order of the other medication when the determination indicates that the at least one returned medication is not usable for completing the order of the other medication.

3. The system of claim 1, wherein the determination of whether the at least one returned medication is usable for completing the order of the other medication is based on the expiration time of the at least one returned medication, the delivery time, an estimated time at which the at least one returned medication will be administered to a patient, and the delivery deadline.

4. The system of claim 3, wherein the one or more processors is further configured to determine the expiration time of the at least one returned medication based on a length of time associated with a known sterility of the at least one returned medication and a length of time associated with a known stability of the at least one returned medication.

5. The system of claim 4, wherein one or more processors is further configured to determine the sterility of the at least one returned medication based on information indicating a contamination level of a preparation location in which the at least one returned medication was initially prepared.

6. The system of claim 1, wherein the one or more processors is further configured to execute the instructions to provide, on the display, an instruction to assist with preparation of the order of the other medication using the at least one returned medication.

7. The system of claim 1, wherein the one or more processors is further configured to execute the instructions to provide an identification of the first location to a device based on a current or a predicted location of the device.

8. The system of claim 1, further comprising an additional scanner associated with the server, wherein the additional scanner is configured to perform scanning the at least one returned medication when the at least one returned medication is delivered to the second location.

9. The system of claim 1, wherein the one or more processors is further configured to execute the instructions to provide a notification indicating at least one of the at least one returned medication is expired, or the at least one returned medication will expire within a threshold time period.

10. The system of claim 9, wherein the notification indicating the at least one returned medication will expire within the threshold time period is based on the expiration time of the at least one returned medication and the delivery time.

11. The system of claim 1, wherein the one or more processors is further configured to execute the instructions to:
  receive an identification of a plurality of returned medications delivered to the second location within a time period, the plurality of returned medications prepared in response to a recurring order to prepare medications that comprises a number of medications to be prepared, wherein the recurring order is for delivery to a third location within the healthcare facility;
  determine, based on at least one of a frequency of return of the plurality of returned medications, a total number of the plurality of returned medications within the time period, and a frequency of expiration of the plurality of returned medications prior to delivery to the third location, whether to modify the recurring order; and
  modify the number of medications to be prepared based on the determination.

12. A method, comprising:
  receiving, at a pharmacy server wirelessly from a portable scanner, first information scanned from a first barcode;
  identifying at least one medication, at a first location within a healthcare facility, to be returned to a second location within the healthcare facility;
  providing, for display at a computing device associated with the first location and remote from the pharmacy server, instructions to retrieve the identified at least one medication from the first location;
  receiving, from a reader device after providing the instructions, at the pharmacy server based on second information scanned from an active identification device affixed to the at least one medication and received wirelessly from the reader device without a scanning action taken by a participant, an indication of the at least one medication and that the at least one medication is available for re-use before it is returned to the second location, wherein the reader device is configured to automatically retrieve the indication via a signal generated and transmitted wirelessly from the active identification device when the active identification device is within a proximity of the reader device;
  receiving, with the pharmacy server, an order for another medication, the order including a delivery deadline and a delivery location;

determining, based on the delivery location and the received indication, a delivery time to deliver the order to the delivery location from the second location;

determining, based on the received indication and the second information, an expiration time of the at least one medication;

determining, with the pharmacy server based on the expiration time of the at least one medication, the delivery time, and the delivery deadline, whether the at least one returned medication is usable for completing the order of the other medication by the delivery deadline; and when the determination indicates that the at least one returned medication is usable for completing the order of the other medication, providing a notification on a display device indicating that the at least one returned medication is usable for completing the order of the other medication.

13. The method of claim 12, further comprising providing a notification indicating to proceed with completing the order of the other medication when the determination indicates that the at least one returned medication is not usable for completing the order of the other medication.

14. The method of claim 12, wherein the determination of whether the at least one returned medication is usable for completing the order of the other medication is based on the expiration time of the at least one returned medication, the delivery time, an estimated time at which the at least one returned medication will be administered to a patient, and the delivery deadline.

15. The method of claim 14, further comprising determining, with the pharmacy server, the expiration time of the at least one returned medication based on a length of time associated with a known sterility of the at least one returned medication and a length of time associated with a known stability of the at least one returned medication.

16. The method of claim 15, wherein determining the sterility of the at least one returned medication comprises determining the sterility based on information indicating a contamination level of a preparation location in which the at least one returned medication was initially prepared.

17. The method of claim 12, further comprising providing an instruction to assist with preparation of the order of the other medication using the at least one returned medication.

18. The method of claim 12, further comprising providing an identification of the first location to a device based on a current or a predicted location of the device.

19. The method of claim 12, wherein receiving the indication that the at least one medication has been returned comprises scanning the at least one returned medication, with an additional scanner associated with the pharmacy server, when the at least one returned medication is delivered to the second location.

20. The method of claim 19, further comprising providing a notification indicating at least one of the at least one returned medication is expired, or the at least one returned medication will expire within a threshold time period.

21. The method of claim 20, wherein the notification indicating the at least one returned medication will expire within the threshold time period is based on the expiration time of the at least one returned medication and the delivery time.

22. The method of claim 12, further comprising:

receiving an identification of a plurality of returned medications delivered to the second location within a time period, the plurality of returned medications prepared in response to a recurring order to prepare medications that comprises a number of medications to be prepared, wherein the recurring order is for delivery to a third location within the healthcare facility;

determining, based on at least one of a frequency of return of the plurality of returned medications, a total number of the plurality of returned medications within the time period, and a frequency of expiration of the plurality of returned medications prior to delivery to the third location, whether to modify the recurring order; and modifying a number of medications to be prepared based on determining the total number.

23. A non-transitory machine-readable medium comprising machine-readable instructions for causing a processor to execute a method for managing a return of a prepared medication, the method comprising:

determining, by a server, at least one medication at a first location within a healthcare facility, to be returned to a second location within the healthcare facility;

providing, for display at a computing device associated with the first location and remote from the server, instructions to retrieve the at least one medication from the first location;

receiving, from a reader device after providing the instructions, based on second information scanned from an active identification device affixed to the at least one medication and received wirelessly from the reader device without a scanning action taken by a participant, an indication that the at least one medication is available for re-use before it is returned to the second location, wherein the reader device is configured to automatically retrieve the indication via a signal generated and transmitted wirelessly from the active identification device when the active identification device is within a proximity of the reader device;

receiving an order for another medication, including a delivery deadline and a delivery location;

determining, based on the delivery location and the received indication, a delivery time to deliver the order to the delivery location from the second location;

determining, based on the received indication and the second information, an expiration time of the at least one medication;

determining, based on the expiration time, the delivery time, and the delivery deadline, whether the at least one returned medication is usable for completing the order of the other medication by the delivery deadline; and when the determination indicates that the at least one returned medication is usable for completing the order of the other medication, providing, to a display device, a notification indicating that the at least one returned medication is usable for completing the order of the other medication.

* * * * *